(12) United States Patent
Del Vecchio

(10) Patent No.: US 10,960,138 B2
(45) Date of Patent: Mar. 30, 2021

(54) VIBRATIONAL TISSUE INJECTION METHODS

(71) Applicant: Daniel A. Del Vecchio, North Attleboro, MA (US)

(72) Inventor: Daniel A. Del Vecchio, North Attleboro, MA (US)

(*) Notice: Subject to any disclaimer, the term of this patent is extended or adjusted under 35 U.S.C. 154(b) by 0 days.

(21) Appl. No.: 16/005,855

(22) Filed: Jun. 12, 2018

(65) Prior Publication Data

US 2018/0289896 A1 Oct. 11, 2018

Related U.S. Application Data

(63) Continuation of application No. 13/897,866, filed on May 20, 2013.

(51) Int. Cl.
*A61M 5/20* (2006.01)
*A61B 17/32* (2006.01)
*A61M 1/00* (2006.01)
*A61B 17/00* (2006.01)

(52) U.S. Cl.
CPC ......... *A61M 5/20* (2013.01); *A61B 17/32002* (2013.01); *A61M 1/0064* (2013.01); *A61B 2017/00398* (2013.01); *A61B 2017/00969* (2013.01); *A61B 2217/005* (2013.01); *A61B 2217/007* (2013.01)

(58) Field of Classification Search
CPC .......... A61M 1/0064; A61M 2205/106; A61M 1/0039; A61B 17/32002; A61B 2217/005; A61B 17/320068
See application file for complete search history.

(56) References Cited

U.S. PATENT DOCUMENTS

| | | | |
|---|---|---|---|
| 4,744,789 A * | 5/1988 | Johnson | A61B 17/34 600/578 |
| 4,815,462 A | 3/1989 | Clark | |
| 5,002,538 A | 3/1991 | Johnson | |
| 5,647,851 A * | 7/1997 | Pokras | A61M 5/20 604/131 |
| 5,681,561 A * | 10/1997 | Hirshowitz | A61K 35/12 424/574 |
| 6,258,054 B1 | 7/2001 | Mozsary et al. | |
| 6,432,710 B1 * | 8/2002 | Boss, Jr. | A61K 35/34 424/422 |
| 6,638,238 B1 | 10/2003 | Weber et al. | |
| 6,942,677 B2 | 9/2005 | Nita et al. | |
| 7,740,632 B2 * | 6/2010 | Young | A61B 17/8822 606/92 |
| 2005/0177071 A1* | 8/2005 | Nakayama | A61B 5/150122 600/583 |
| 2006/0206098 A1 | 9/2006 | Fard | |
| 2006/0224144 A1 | 10/2006 | Lee | |
| 2010/0152614 A1 | 6/2010 | Mark | |
| 2014/0114234 A1* | 4/2014 | Redding, Jr. | A61M 37/0092 604/22 |

* cited by examiner

*Primary Examiner* — William R Carpenter

(74) *Attorney, Agent, or Firm* — R. Keith Harrison

(57) ABSTRACT

Methods of injecting tissue into a recipient site on a patient may include obtaining at least one tissue, vibrating the at least one tissue and simultaneously injecting the at least one tissue into the recipient site on the patient.

14 Claims, 1 Drawing Sheet

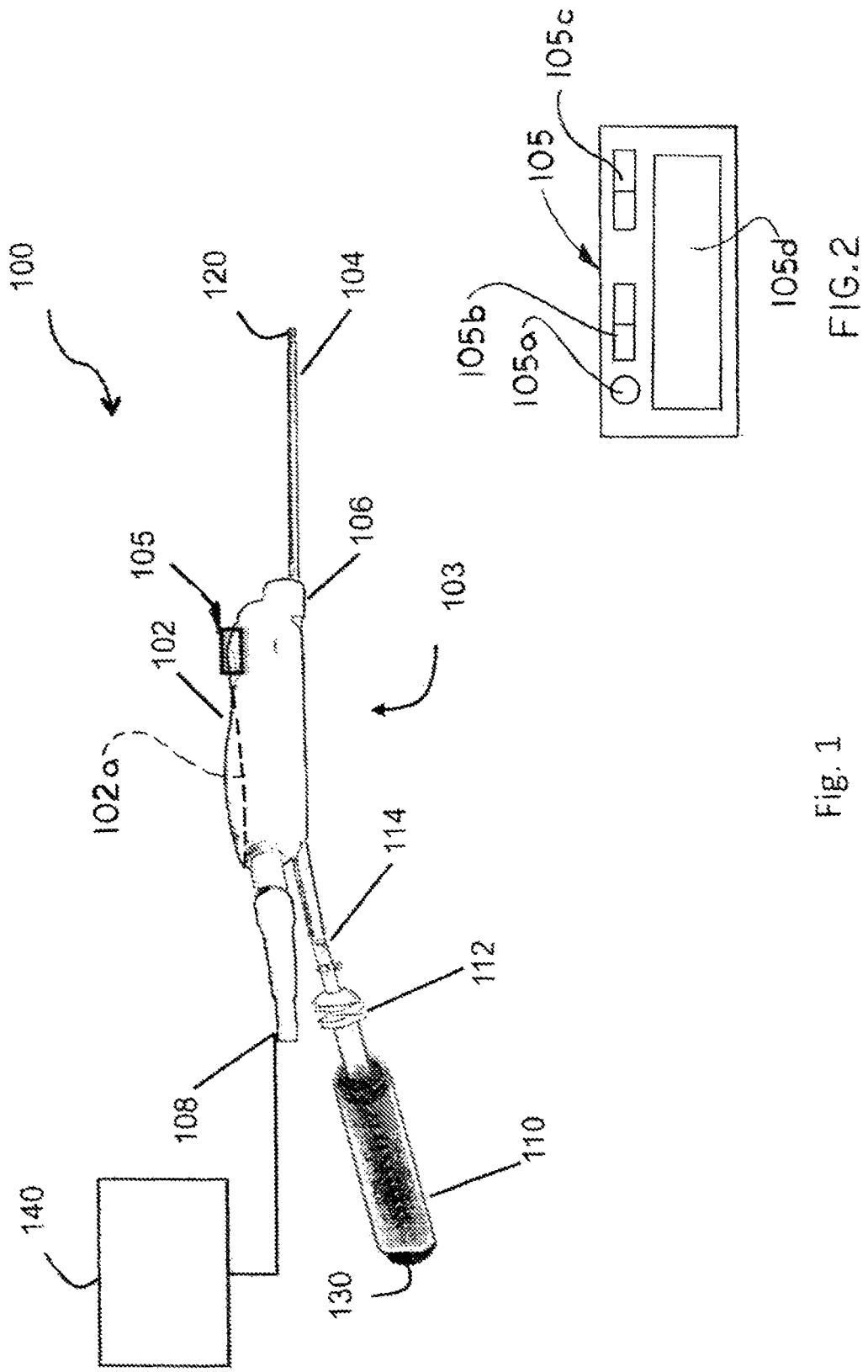

VIBRATIONAL TISSUE INJECTION METHODS

RELATED APPLICATIONS

This application is a continuation application of U.S. application Ser. No. 13/897,866, filed May 20, 2013 and entitled A VIBRATIONAL DEVICE FOR FAT INSERTION DURING FAT TRANSPLANTATION, which claims the benefit of U.S. App. No. 61/649,488 filed May 2, 2012, the entire content of each of which applications is hereby incorporated by reference.

BACKGROUND

Cannulas are surgical instruments, generally formed as tubes, used for delivery or removal of fluid and the like from a body. In cosmetic surgery, a cannula can be used to harvest fat or other tissue, and/or to inject fat or other tissue.

There remains a need for improved injection cannulas.

SUMMARY

An injection cannula includes a hand-held mechanical motorized device to improve delivery of fat and facilitate dispersion at a recipient site. The injection cannula may, for example be a cannula for injecting fat in a cosmetic surgical procedure for fat transplantation such as percutaneous injection or injection directly into the subcutaneous fat. An electric motor, pneumatic motor, or other mechanism may be used to provide vibration.

BRIEF DESCRIPTION OF THE FIGURES

The invention and the following detailed description of certain embodiments thereof may be understood by reference to the following FIGURES.

FIG. 1 shows a hand-held mechanical motorized injection cannula device and

FIG. 2 shows a typical control suitable for implementation of the motorized injection cannula device.

DETAILED DESCRIPTION

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus the term "or" should generally be understood to mean "and/or" and so forth.

Disclosed herein is a cannula connected to a hand-held mechanical motorized device for use in cosmetic surgical procedures such as all types of fat injection, including percutaneous injection or injection directly into the subcutaneous fat, during fat transplantation. However, it will be understood that the invention disclosed herein is not so limited, and the inventive concept may be adapted to other tissue injection procedures or the like.

FIG. 1 shows a hand-held mechanical motorized injection cannula device. The device 100 may include a motor 102, an injection cannula 104, a connector 106, a motor power source connection 108, a syringe 110, a lock thread connector 112, and a syringe to hose connector 114.

The motor 102 may be shaped to be comfortably held by a user during all types of fat injection, including percutaneous injection or injection directly into the subcutaneous fat, during fat transplantation, or the vibrating motor 102 may be positioned away from a gripping portion 103 of the device 100 in any location suitable for transmitting vibrational forces to a tip 120 of the injection cannula 104. In general, the gripping portion 103 may be shaped and sized for gripping by a human hand, and more particularly for being held by a surgeon in any desired grip and orientation for a particular injection procedure.

The motor 102 may be constructed with a housing using, either individual or in combination, plastic materials, metals, or other appropriate material. The motor 102 may include vibration-absorbing materials positioned between the motor 102 and the gripping portion 103 to reduce the motor vibration transmitted to the user's hand, that is, to isolate vibrational forces between the motor 102 and the gripping portion 103 while at the same time being more directly mechanically coupled to the injection cannula 104.

The motor 102 may include a control 105 such as buttons, switches, slides, triggers, or other input control devices to allow the user to control the operation of the hand-held mechanical motorized injection cannula device 100. By way of a non-limiting example, the vibration motor 102 may include a button to turn the vibration motor 102 on and off, a slide switch to control the motor speed, a slide switch to control vibration amplitude, or other input control devices that may control the characteristics of the vibration motor 102. The control 105 may also include a display to provide status information, an indication of vibrational intensity (rate and/or amplitude), or any other useful information.

In another aspect, the device 100 may include a pump 130 to actively control a delivery rate of fat or other material. This may include a thumb-operated plunger, or this may include any suitable electro-mechanical device for automatically delivering material at a controlled rate. In one aspect, the control 105 may include one or more buttons or the like to control a rate of delivery of material from the syringe 110.

The vibrating motor 102 may include any electric motor, pneumatic motor, or other electro-mechanical device that uses, e.g., an eccentricity or other mechanism to create vibration. Regardless of the type of motor 102, a power source 140 for the motor 102 may be connected at the motor power source connection 108. In one example, if the motor 102 uses an electric motor, the power supply connection 108 may include any suitable wires, plugs, and so forth. In another example, if the motor 102 uses an air compressor motor, a compressed air line may be connected to the motor power source connection 108. The compressed air line maybe connected using any typically available air line connector, such as, but not limited to, a quick connect/disconnect connector. In another aspect the power source 140 may be integrated into the gripping portion 103 or other housing of the device 100 for independent operation of the device 100.

At an output of the motor 102, the injection cannula 104 may be connected to the motor 102 using the connector 106. The injection cannula 104 may be any needle typically used for fat or tissue injection procedures or the like. The connector 106 may be a twist type connector, Luer lock, or any other coupling that securely affixes the injection cannula 104 to the motor 102 and transmits vibrational energy from the motor to the injection cannula 104.

At the proximal end of the vibrating motor 102, a syringe 110 such as a Toomey syringe may be connected to the motor 102 using the locked thread connector 112 and the syringe to hose connector 114. In an embodiment, the syringe 110 may contain the fat or other tissue to be injected during a procedure. The syringe 110 may be coupled in fluid communication to the injection cannula 104 through the vibration motor 102 using a hose cannula or the like. The user may control the injection flow of fat or other tissue through the injection cannula 104 from the syringe 110 using, e.g., a thumb plunger or other automated or mechanical delivery system.

Depending upon the application, the injection cannula 104 may include a trocar or the like to facilitate injection. The tip 120 of the injection cannula 104 may also or instead include a sharpened point or other cutting surface to facilitate skin puncture.

In an embodiment, the device 100 may be used in fat injection, including percutaneous injection or injection directly into the subcutaneous fat, during fat transplantation. In a procedure using the device, a user can control injection or delivery rate of material in the syringe 110, and may concurrently control vibration characteristics of the motor for desired flow and distribution characteristics.

In an embodiment, the vibration characteristics of the vibrating motor 102 may be used to cause the injection cannula 104 to vibrate, and therefore may facilitate the flow of fat and egress of fat from the injection cannula 104 during fat injection, including percutaneous injection or injection directly into the subcutaneous fat, during fat transplantation. By way of a non-limiting example, while applying a steady pressure to the syringe 110, the user may increase the flow of fat or other tissue from the injection cannula 104 by increasing the vibration frequency of the vibrating motor 102. In another example, the user may increase the flow of fat or other tissue from the injection cannula 104 by increasing vibration amplitude of the vibrating motor 102.

In another embodiment, the hand-held mechanical motorized injection cannula device 100 vibration of the injection cannula 104 may facilitate the dispersion of fat into the recipient site during fat injection, including percutaneous injection or injection directly into the subcutaneous fat, during fat transplantation. By way of a non-limiting example, the vibration of the injection cannula 104 may move the tip of the injection cannula 104 within an increased space volume compared to a non-vibrating cannula, and therefore may disperse injected fat or other tissue into an increased uniform volume at the recipient site. As the user changes either the vibration frequency or the vibration amplitude, the space volume defined by movement of the tip 120 of the injection cannula 104 may change, resulting in a corresponding change in the injection space volume of the recipient site. Adjusting the vibration characteristics of the motor 102 may also control the flow and/or distribution of injected fat at a recipient site.

In an embodiment, the hand-held mechanical motorized injection cannula device 100 vibration of the injection cannula 104 may create a larger number of individual channels within a recipient site in which to disperse fat or other tissue, and therefore increasing the dispersion of fat grafts in all types of fat injection, including percutaneous injection of injection directly into the subcutaneous fat, during fat transplantation. As the user adjusts the vibration characteristics of the vibration motor 102 (vibration frequency or amplitude), the injection cannula 104 may create individual channels at the recipient site that are in proportion to the vibration characteristics of the vibration motor 02. As the user increases either the vibration frequency or amplitude, an increased number of individual channels at the recipient site may also be created in which fat or other tissue may be injected.

While particular embodiments of the present invention have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method of injecting fat into subcutaneous fat at a recipient site in a tissue on a patient in a fat transplantation procedure to facilitate lipofilling of the tissue, comprising:
   obtaining fat from the patient;
   vibrating the fat;
   simultaneously percutaneously injecting the fat into the subcutaneous fat at the recipient site on the patient; and
   actively controlling flow of the fat into the subcutaneous fat at the recipient site by selectively increasing or decreasing at least one of vibration frequency and vibration amplitude of the fat to move the fat within a selected space volume in the recipient site of the tissue to control and optimize flow and distribution of the fat in the recipient site and achieve an optimal combination of controlled dispersal of the fat in the tissue while maintaining cosmetic plumping and sculpting of the tissue.

2. The method of claim 1 wherein vibrating the fat comprises controlling vibration frequency of the fat.

3. The method of claim 1 wherein vibrating the fat comprises controlling vibration amplitude of the fit.

4. The method of claim 1 wherein vibrating the fat comprises controlling vibration frequency and vibration amplitude of the fat.

5. The method of claim 1 wherein vibrating the fat comprises vibrating the fat using an eccentricity mechanism.

6. The method of claim 5 wherein vibrating the fat using an eccentricity mechanism comprises vibrating the fin using at least one of an electric motor and a pneumatic motor.

7. A method of injecting fat into subcutaneous fat at a recipient site on a patient in a fat transplantation procedure to facilitate lipofilling of the tissue, comprising:
   obtaining, a hand-held mechanical motorized injection cannula device including:
      a gripping portion;
      an injection cannula extending from the gripping portion, the injection cannula having a tip; and
      a motor carried by the gripping portion, the motor directly mechanically coupled to the injection cannula to impart vibration to the tip of the injection cannula;
   obtaining fat from the patient;
   creating individual channels in the subcutaneous fat at the recipient site in proportion to vibration characteristics of the vibration motor by vibrating the tip of the injection cannula by operation of the motor;
   simultaneously injecting the fat through the injection cannula into the subcutaneous fat at the recipient site on the patient; and
   actively controlling flow of the fat into the subcutaneous fat at the recipient site by selectively increasing or decreasing at least one of vibration frequency and vibration amplitude of the tip of the injection cannula to move the fat within a selected space volume of the individual channels in the recipient site of the tissue to control and optimize flow and distribution of the fat in the recipient site and achieve an optimal combination of controlled dispersal of the fat in the tissue while maintaining cosmetic plumping and sculpting of the tissue.

8. The method of claim 7 wherein vibrating the tip of the injection cannula comprises controlling vibration frequency of the tip of the injection cannula.

9. The method of claim 7 wherein vibrating the tip of the injection cannula comprises controlling vibration amplitude of the tip of the injection cannula.

10. The method of claim 7 wherein vibrating the tip of the injection cannula comprises controlling vibration frequency and vibration amplitude of the tip of the injection cannula.

11. The method of claim 7 wherein vibrating the lip of the injection cannula by operation of the motor comprises vibrating the tip of the injection cannula by operation of a motor using an eccentricity mechanism to create vibration.

12. The method of claim 1 wherein vibrating the tip of the injection cannula by operation of a motor using an eccentricity mechanism to create vibration comprises vibrating the tip of the injection cannula by operation of at least one of an electric motor and a pneumatic motor using an eccentricity mechanism to create vibration.

13. A method of injecting fat into subcutaneous fin at a recipient site on a patient in a fat transplantation procedure to facilitate lipofilling the tissue, comprising:
   obtaining a hand-held mechanical motorized injection cannula device including:
      a gripping portion;
      an injection cannula extending from the gripping portion, the injection cannula having a tip;
      a motor carried by the gripping portion, the motor directly mechanically coupled to the injection cannula to impart vibration to the injection cannula; and
      a syringe disposed in fluid communication with the injection cannula;
   obtaining fat from the patient;
   placing the fat in the syringe;
   creating individual channels in the subcutaneous fat at the recipient site in proportion to vibration characteristics of the vibration motor by vibrating the tip of the injection cannula by operation of the motor;
   simultaneously injecting the fat from the syringe through the injection cannula into the subcutaneous fat at the recipient site on the patient; and
   selectively increasing or decreasing flow of the fat into the subcutaneous fat at the recipient site by actively controlling at least one of vibration frequency and vibration amplitude of the tip of the injection cannula as the fat is injected into the subcutaneous fat at the recipient site to move the fat within a selected space volume of the individual channels in the recipient site of the tissue to control and optimize flow and distribution of the fat in the recipient site and achieve an optimal combination of controlled dispersal of the fat in the tissue while maintaining cosmetic plumping and sculpting of the tissue.

14. The method of claim 13 wherein vibrating the tip of the injection cannula by operation of the motor comprises vibrating the tip of the injection cannula by operation of a motor using an eccentricity mechanism to create vibration.

* * * * *